(12) United States Patent
Schnatterer et al.

(10) Patent No.: US 11,384,061 B2
(45) Date of Patent: Jul. 12, 2022

(54) PROCESS FOR PREPARING ESTERS OF N-ACYLATED AMINO ACIDS WITH ACID-LABILE KETO PROTECTIVE GROUP FUNCTIONS

(71) Applicant: Bayer Aktiengesellschaft, Leverkusen (DE)

(72) Inventors: Albert Schnatterer, Leverkusen (DE); Michael Dockner, Cologne (DE); Peter Bruechner, Krefeld (DE); Thomas Himmler, Odenthal (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 0 days.

(21) Appl. No.: 17/047,994

(22) PCT Filed: Apr. 15, 2019

(86) PCT No.: PCT/EP2019/059641
§ 371 (c)(1),
(2) Date: Oct. 15, 2020

(87) PCT Pub. No.: WO2019/201842
PCT Pub. Date: Oct. 24, 2019

(65) Prior Publication Data
US 2021/0139450 A1 May 13, 2021

(30) Foreign Application Priority Data
Apr. 17, 2018 (EP) .................................. 18167708

(51) Int. Cl.
*C07D 317/72* (2006.01)
*C07D 491/113* (2006.01)

(52) U.S. Cl.
CPC ........ *C07D 317/72* (2013.01); *C07D 491/113* (2013.01)

(58) Field of Classification Search
CPC .......................... C07D 317/72; C07D 491/113
See application file for complete search history.

(56) References Cited

U.S. PATENT DOCUMENTS

| | | | |
|---|---|---|---|
| 5,770,732 A | 6/1998 | Hirschmann et al. | |
| 6,589,976 B1 | 7/2003 | Fischer et al. | |
| 7,897,543 B2* | 3/2011 | Bretschneider | A01N 43/24 504/140 |
| 2010/0120727 A1 | 5/2010 | Xu | |
| 2011/0190493 A1 | 8/2011 | Bretschneider et al. | |
| 2019/0202837 A1* | 7/2019 | Himmler | C07D 317/72 |
| 2021/0032262 A1* | 2/2021 | Himmler | C07C 233/52 |

FOREIGN PATENT DOCUMENTS

| | | | |
|---|---|---|---|
| DE | 197 42 492 A1 | 4/1999 | |
| EP | 3301092 A2 * | 4/2018 | ........... C07D 491/10 |
| WO | 02/055481 A1 | 7/2002 | |
| WO | 2006/089633 A2 | 8/2006 | |
| WO | 2018/024659 A1 | 2/2018 | |
| WO | WO-2018024659 A1 * | 2/2018 | ........... C07D 319/08 |

OTHER PUBLICATIONS

PCT International Search Report for PCT/EP2019/059641, dated Aug. 2, 2019.
March, J., Advanced Organic Chemistry, 3rd edition, John Wiley & Sons (1985), p. 354.
Markad, et al., "D-Glucose based synthesis of proline-serine C-C linked central and right hand core of a kaitocephalin-a glutamate receptor antagonist," RSC Advances, (2015), vol. 5: 81162-81167.
Wang, et al, "Facile Synthesis of Amino Acid and Peptide Esters under Mild Conditions via Cesium Salts," J. Org. Chem., (1977), vol. 42, No. 8: 1286-1290.
Creighton, et al., "Mechanistic Studies of an Unusual Amide Bond Scission," J. Am. Chem. Soc., (1999), vol. 121:6786-6791.
Houben-Weyl, XI/2, S. 355 ff, with English translation.

* cited by examiner

Primary Examiner — Matthew P Coughlin
(74) Attorney, Agent, or Firm — McBee Moore & Vanik IP, LLC

(57) ABSTRACT

The present invention relates to a novel process for the esterification of N-acylated amino acids which contain an acid-labile keto protective group under alkaline conditions without using a polar aprotic solvent, in which the N-acylated amino acid with acid-labile keto protective group prepared in situ is esterified using an alkyl halide or a mono- or dialkyl ester of sulfuric acid.

4 Claims, No Drawings

PROCESS FOR PREPARING ESTERS OF N-ACYLATED AMINO ACIDS WITH ACID-LABILE KETO PROTECTIVE GROUP FUNCTIONS

CROSS-REFERENCE TO RELATED APPLICATIONS

This application is the National Stage entry of International Application No. PCT/EP2019/059641, filed 15 Apr. 2019, which claims priority to European Patent Application No. 18167708.9, filed 17 Apr. 2018.

BACKGROUND

Field

The present invention relates to a novel process for preparing esters of N-acylated amino acids from N-acylated amino acids which contain an acid-labile keto protective group and readily available organic alkylating reagents. The esters of N-acylated amino acids serve as precursors for the preparation of crop protection compositions with insecticidal, acaricidal or herbicidal action (for example WO 06/089633).

Description of Related Art

It is already known that amino acids react with alcohols in the presence of hydrogen chloride to give the corresponding amino acid esters (Houben-Weyl, XI/2, S. 355 ff). However, this general preparation method fails when the amino acids contain acid-labile protective groups which are cleaved off under these reaction conditions.

In such cases, the already known method is applied according to which amino acids are esterified in a polar aprotic solvent using an alkylating reagent in the presence of a base. Thus, e.g., Dhavale et al. (*RSC Advances* 5, 81165 (2015)) use methyl iodide as alkylating reagent, potassium hydrogencarbonate as base and N,N-dimethylformamide (DMF) as solvent for the preparation of the methyl ester of (1,2-O-isopropylidene-3-O-tosyl-5-deoxy-5-C(S)-(2(5-oxopyrrolidine))-α-D-glucohexofurano)uronic acid. According to WO 02/055481 and US005770732, the use of potassium carbonate instead of potassium hydrogencarbonate is also customary. Meienhofer et al. (*J. Org. Chem.* 42, 1286 (1977)) describe the use of the highly expensive caesium carbonate as base.

The examples from the literature show that the application of these esterification methods is restricted to the use of a polar aprotic solvent and a weak base. However, the use of typical polar aprotic solvents such as DMF or N,N-dimethylacetamide (DMAC) has the drawback that these solvents can commonly only be recovered using expensive methods, and yet because of their relatively high price, such recovery is however desirable for economic reasons.

It is also already known to use potassium hydroxide, which is a stronger base in comparison to potassium hydrogencarbonate and potassium carbonate. In this case, however, according to Creighton et al. (*J. Am. Chem. Soc.* 121, 6786 (1999)), not only the oxygen of the carboxyl group but also the nitrogen of the amino acid, protected here by a tert-butyloxycarbonyl (Boc) group, is alkylated.

Furthermore, the methods for esterification of carboxylic acids with diazoalkane described in textbooks of organic chemistry (e.g. *J. March, Advanced organic chemistry*, 3rd edition, John Wiley & Sons 1985, p. 354, ISBN 0-471-85472-7) can be applied to amino acids, as is known inter alia from US20100120727. Yet, for safety-related and economical reasons, diazoalkanes are essentially only used in the laboratory, and are hardly considered for large-scale technical use.

There was accordingly still a need to provide a more widely applicable, safer and economical technical process for preparing esters of N-acylated amino acids bearing acid-labile keto protective groups.

SUMMARY

Surprisingly, it has now been found that the esterification of N-acylated amino acids which contain an acid-labile keto protective group under alkaline conditions is possible without using a polar aprotic solvent, by the N-acylated amino acid with acid-labile keto protective group prepared in situ being esterified using an alkyl halide or a mono- or dialkyl ester of sulfuric acid.

Thus, the present invention provides a novel process for preparing compounds of the general formula (I)

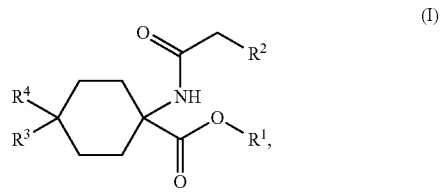

in which
R¹ is straight-chain or branched $C_1$-$C_6$ alkyl or benzyl,
R² is straight-chain or branched $C_1$-$C_6$ alkyl or phenyl optionally substituted by methyl, ethyl, fluorine, chlorine, methoxy or ethoxy,
R³ and R⁴ independently of one another are an OR⁵ or SR⁵ radical or together are an —O(CHR⁶)$_n$O— radical or together are an =NR⁷ radical,
wherein
R⁵ is straight-chain or branched $C_1$-$C_6$ alkyl,
R⁶ is hydrogen, methyl, ethyl or phenyl,
n is 2 or 3,
R⁷ is straight-chain or branched $C_1$-$C_6$ alkyl, phenyl, benzyl or 4-methoxybenzyl,
characterized in that in a first step (1) amino acid salts of the general formula (II)

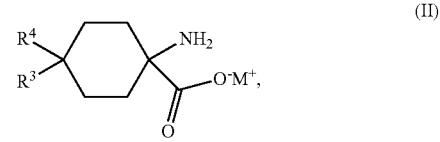

in which
M is sodium, potassium or an NR⁸$_4$ group,
wherein
R⁸ is hydrogen or straight-chain or branched $C_1$-$C_6$ alkyl
and
R³ and R⁴ have the definition given above, are reacted with carbonyl halides of the general formula (III)

in which

Y is fluorine, chlorine or bromine, and

R² has the meaning given above, to give N-acylated amino acid salts of the general formula (IV)

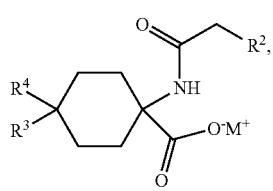

(IV)

in which

M, R², R³ and R⁴ have the definitions given above, in the presence of a base and a solvent or solvent mixture, which is not polar aprotic, and subsequent thereto in a second step (2) of the inventive process, the N-acylated amino acids of the general formula (IV) are reacted with an alkylating reagent of the general formula (V) or (VI) in the presence of a base and a solvent or solvent mixture, which is not polar aprotic, to give the compounds of the general formula (I).

DETAILED DESCRIPTION OF A PREFERRED EMBODIMENT

As alkylating reagents, use may be made of alkyl halides of the general formula (V) or sulfuric acid di- or monoesters or salts of the sulfuric acid monoester of the general formula (VI)

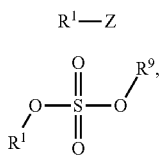

in which

R¹ has the definition given above,

Z is chlorine, bromine or iodine and

R⁹ is hydrogen, sodium, potassium or the radical R¹.

The compounds of the formula (II) and (III) are either commercially available or can be prepared by known processes.

The compounds of the formulae (V) and (VI) are commercially available.

The inventive process is depicted by Scheme 1.

Scheme 1

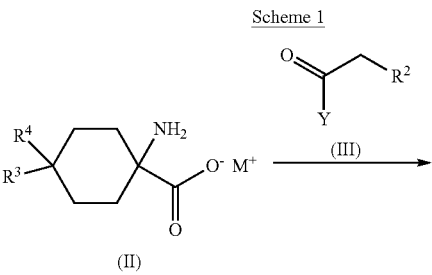

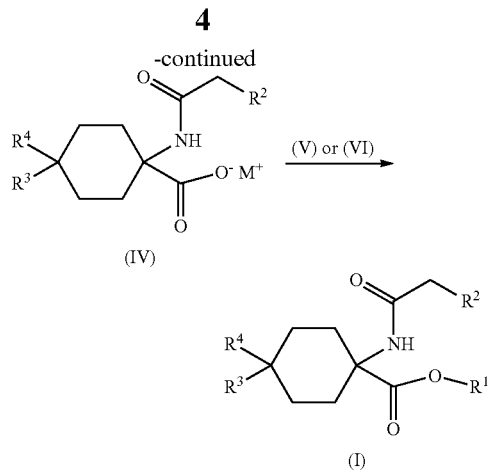

Preference is given to the process for preparing compounds of the general formula (I), wherein R¹ is methyl, ethyl, n-propyl, n-butyl or benzyl, R² is phenyl, optionally substituted by methyl, ethyl, chlorine, methoxy or ethoxy, R³ and R⁴ independently of one another are an OR⁵ radical or together are an —O(CHR⁶)ₙO— radical or together are an =NR⁷ radical, R⁵ is straight-chain C₁-C₆-alkyl, R⁶ is hydrogen, methyl, ethyl or phenyl, n is 2 or 3, R⁷ is straight-chain or branched C₁-C₆ alkyl, phenyl, benzyl or 4-methoxybenzyl, M is sodium or potassium, Y is fluorine or chlorine, Z is chlorine, bromine or iodine, R⁹ is hydrogen, sodium, potassium or the radical R¹.

Particular preference is given to the process for preparing compounds of the general formula (I), wherein R¹ is methyl, ethyl, n-propyl or n-butyl, R² is phenyl, optionally substituted by methyl, ethyl or chlorine, R³ and R⁴ are an OR⁵ radical or together are an —O(CH₂)₂O— radical, R⁵ is methyl, ethyl, n-propyl or n-butyl, M is sodium or potassium, Y is chlorine, Z is bromine or iodine, R⁹ is hydrogen, sodium, potassium or the radical R¹.

Emphasis is given to the process for preparing the compound of the formula (I-1,)

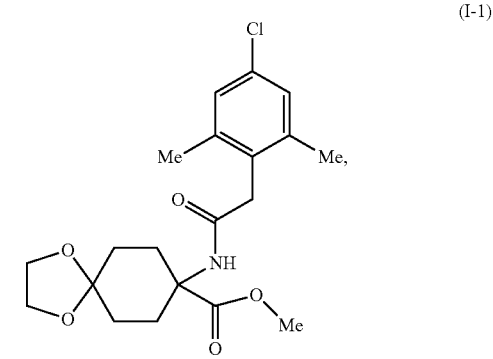 [SMILES: COC(=O)C1(NC(=O)Cc2c(C)cc(Cl)cc2C)CCC2(CC1)OCCO2]

characterized in that in a first step (1) the amino acid salt of the general formula (II-1)

(II-1)

[Structure: 1,4-dioxaspiro[4.5]decane with NH₂ and C(=O)O⁻M⁺ substituents]

in which
M is sodium or potassium,
is reacted with the carbonyl halide of the formula (III-1)

(III-1)

[Structure: 4-chloro-2,6-dimethylphenyl-CH₂-C(=O)Cl]

to give N-acylated amino acid salts of the general formula (IV-1)

(IV-1)

[Structure: 4-chloro-2,6-dimethylphenyl-CH₂-C(=O)NH- attached to 1,4-dioxaspiro[4.5]decane with C(=O)O⁻M⁺]

in which
M is sodium or potassium,
in the presence of a base and a solvent or solvent mixture, which is not polar aprotic, and subsequent thereto in a second step (2) of the inventive process, the N-acylated amino acids of the general formula (IV-1) are reacted with dimethyl sulfate (compound of the formula (VI-1), in which R¹ and R⁹ are methyl) in the presence of a base and a solvent or solvent mixture, which is not polar aprotic, to give the compound of the formula (I-1).

The present invention likewise provides novel compounds of the general formula (I-a)

(I-a)

[Structure: 4-chloro-2,6-dimethylphenyl-CH₂-C(=O)NH- attached to cyclohexane bearing R³, R⁴ and C(=O)OR¹]

in which
R¹ is methyl, ethyl, n-propyl, n-butyl or benzyl, and
R³ and R⁴ are an OR⁵ radical or together are an —O(CH₂)₂O— radical, wherein
R⁵ is methyl, ethyl, n-propyl or n-butyl,
wherein, if R¹ is methyl, then R⁵ is not methyl,
wherein, if R¹ is methyl, then R³ and R⁴ are not together a radical —O(CH₂)₂O—.

Preference is given to novel compounds of the general formula (I-a), in which
R¹ is ethyl, n-propyl or n-butyl, and
R³ and R⁴ are together an —O(CH₂)₂O— radical.

The present invention likewise provides novel compounds of the general formula (IV-1)

(IV-1)

[Structure: 4-chloro-2,6-dimethylphenyl-CH₂-C(=O)NH- attached to 1,4-dioxaspiro[4.5]decane with C(=O)O⁻M⁺]

in which
M is sodium or potassium.

There follows a detailed elucidation of the process according to the invention:

Specifically, the inventive process will be carried out such that, in the first step (1), firstly amino acid salts of the general formula (II) are dissolved in water or an aqueous solution of a base or these amino acid salts of the general formula (II) are produced by the corresponding free amino acids or salts of the amino acids being dissolved with acids such as hydrochlorides, sulfates or hydrosulfates in an aqueous solution of a base.

Examples of useful bases include lithium carbonate, sodium carbonate, sodium hydrogencarbonate, potassium carbonate, potassium hydrogencarbonate, lithium hydroxide, sodium hydroxide or potassium hydroxide or mixtures of these bases. Use is preferably made of sodium carbonate, sodium hydrogencarbonate, potassium carbonate, potassium hydrogencarbonate, sodium hydroxide or potassium hydroxide or mixtures of these bases.

The amount of base is selected such that a pH of 8 to 14 is established. Preferably, a pH of 10.5 to 12.5 is established.

It may optionally be necessary to adjust the pH to the desired range by subsequent addition of an inorganic acid. Useful inorganic acids include hydrochloric acid or sulfuric acid, preferably hydrochloric acid.

Subsequently, in this first step (1) of the inventive process, the aqueous solution of the amino acid salts of the general formula (II) is reacted with a carbonyl halide of the general formula (III) to give an N-acylated amino acid salt of the general formula (IV).

The amount of carbonyl halide of the general formula (III) in this case is 0.9 to 1.5 molar equivalents, based on the amino acid salt of the general formula (II). Preference is given to using 1.0 to 1.25 molar equivalents.

The carbonyl halide of the general formula (II) is either added in liquid form without using a solvent or as a solution in a solvent which is inert under the reaction conditions. Examples of useful solvents include toluene, o-xylene, m-xylene, p-xylene, mesitylene, chlorobenzene, 1,2-dichlorobenzene, anisole, cyclohexane, methylcyclohexane, pentane, heptane, isooctane or mixtures of these solvents. Use is preferably made of toluene, o-xylene, m-xylene, p-xylene, mesitylene, chlorobenzene, anisole, methylcyclohexane, heptane, isooctane or mixtures of these solvents. Use is particularly preferably made of toluene.

If required in order to maintain the desired pH, further aqueous base solution is metered in simultaneously to the metering in of the carbonyl halide of the general formula (III). In this case, either equimolar amounts of base are metered in in parallel to the carbonyl halide, or the reaction is carried out under pH control and the metering in of the base is adapted accordingly.

The first step (1) of the process according to the invention is for example carried out at a temperature of between 0 and 100° C.; preferably between 10 and 70° C.

The N-acylated amino acid salts of the general formula (IV) may be isolated or the aqueous solutions of the N-acylated amino acid salts of the general formula (IV) are used without work-up in the second step of the inventive process. Preference is given to using the aqueous solutions without further work-up.

If it is intended to isolate the N-acylated amino acid salts of the general formula (IV), this may for example be carried out by concentrating the aqueous solutions under reduced pressure. One method of the inventive process for isolating the N-acylated amino acid salts of the general formula (IV) consists of increasing the cation concentration (sodium or potassium) in the solution by addition of, for example, sodium hydroxide, sodium carbonate, sodium hydrogencarbonate, sodium chloride, sodium sulfate, potassium hydroxide, potassium carbonate, potassium hydrogencarbonate, potassium chloride or potassium sulfate. As a result, this leads either to the formation of a second aqueous phase which contains the N-acylated amino acid salt, or the N-acylated amino acid salt precipitates out and can be filtered off.

In the second step (2) of the inventive process, the N-acylated amino acid salts of the general formula (IV) are reacted with an alkylating agent of the general formula (V) or (VI) to give the amino acid esters of the general formula (I). Preference is given to using dimethyl sulfate as alkylating agent.

The alkylating agent is used in amounts from 1 to 5 molar equivalents, based on the N-acylated amino acid salt of the general formula (IV). Preference is given to using 1.5 to 2.5 molar equivalents.

During the metering in of the alkylating agent of the general formula (V) or (VI), the pH of the reaction mixture is kept at between 8 to 14, preferably at between 8 to 12.5, by the simultaneous addition of a base.

Examples of useful bases include lithium carbonate, sodium carbonate, sodium hydrogencarbonate, potassium carbonate, potassium hydrogencarbonate, lithium hydroxide, sodium hydroxide or potassium hydroxide or mixtures of these bases. Use is preferably made of sodium carbonate, sodium hydrogencarbonate, potassium carbonate, potassium hydrogencarbonate, sodium hydroxide or potassium hydroxide or mixtures of these bases.

The reaction temperature in the second step (2) of the inventive process can be varied within wide limits. On the one hand, the reaction temperature will be chosen to be as high as possible in order to achieve a rapid and complete reaction. On the other hand, the reaction temperature will be chosen to be low enough that, as far as possible, alkaline hydrolysis of the N-acylated amino acid ester of the general formula (I) formed does not occur. Accordingly, the reaction temperature also depends on the pH chosen in the second step (2) of the inventive process. It is typically between 0 and 120° C., preferably between 15 and 90° C.

The second step (2) of the inventive process may be carried out either without, or in the presence of, a phase transfer catalyst. The reaction is preferably carried out with the use of a phase transfer catalyst.

The amount of phase transfer catalyst is typically between 0.01 and 0.2 molar equivalents, preferably between 0.08 and 0.12 molar equivalents.

The following may be mentioned as examples of typical phase transfer catalysts: tri-n-butyl-n-tetradecylphosphonium chloride, tetraphenylphosphonium bromide, tetrabutylammonium bromide, tetrabutylammonium hydrogen sulfate, tetraoctylammonium chloride or tetradecylammonium chloride or mixtures of such tetraalkylammonium salts, such as Aliquat336.

Use is preferably made of tri-n-butyl-n-tetradecylphosphonium chloride, tetraoctylammonium chloride such as Aliquat 336, tetradecylammonium chloride or mixtures of these tetraalkylammonium salts. Use is particularly preferably made of Aliquat 336.

The second step (2) of the inventive process, as well as being carried out at normal pressure, may also be carried out at reduced or also increased pressure.

The selection of the work-up methods is determined by the properties of the amino acid ester prepared.

The present invention is illustrated in more detail by the examples which follow without being restricted thereby.

EXAMPLES

Example 1 sodium 8-[2-(4-chloro-2,6-dimethylphenyl)acetamido]-1,4-dioxaspiro[4.5]decane-8-carboxylate

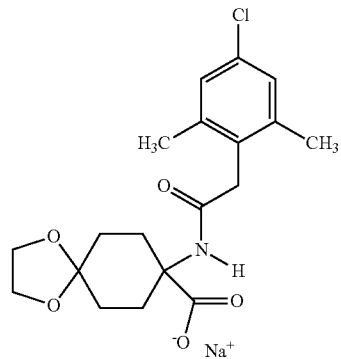

A solution of 47.3 g of sodium 8-amino-1,4-dioxaspiro[4.5]decane-8-carboxylate of a purity of 70.8% (corresponding to 150 mmol; the remainder is essentially sodium carbonate and sodium hydroxide) in 108 ml of water is initially charged in a 600 ml reaction vessel with overhead stirrer, pH electrode and metering unit. The pH of the slightly cloudy solution is 12.9. The mixture is cooled to 10° C. and the pH is adjusted to 11.8 by addition of 10% hydrochloric acid. A solution of 36.5 g [168 mmol] of (4-chloro-2,6-dimethylphenyl)acetyl chloride in 23 ml of toluene is subsequently metered in within one hour. At the same time, 25.1 g of 32% sodium hydroxide solution [201 mmol NaOH] is metered in such that the pH remains constant at 11.8. After the metering in has been completed, stirring is carried out for a further hour at 10° C., the mixture is allowed to return to room temperature, and the phases are separated. This gives 220 g of a cloudy yellow solution, which can be used in the next step without further work-up. HPLC analysis (acid) shows a proportion of 75.4% of 8-[2-(4-chloro-2,6-dimethylphenyl)acetamido]-1,4-dioxaspiro[4.5]decane-8-carboxylic acid (alongside 24.0% 4-chloro-2,6-dimethylphenylacetic acid and 0.1% toluene).

Example 2 sodium 8-[2-(4-chloro-2,6-dimethylphenyl)acetamido]-1,4-dioxaspiro[4.5]decane-8-carboxylate

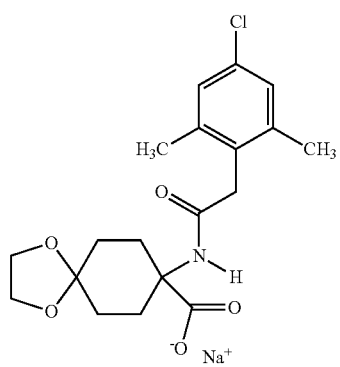

A solution of 18.92 g of sodium 8-amino-1,4-dioxaspiro[4.5]decane-8-carboxylate of a purity of 70.8% (corresponding to 60 mmol; the remainder is essentially sodium carbonate and sodium hydroxide) in 43 ml of water is initially charged in a 100 ml reaction vessel with overhead stirrer, pH electrode and metering unit. The mixture is cooled to 10° C. and the pH is adjusted to 11.8 by addition of 10% hydrochloric acid. A solution of 14.33 g [66 mmol] of (4-chloro-2,6-dimethylphenyl)acetyl chloride in 7.5 ml of toluene is subsequently metered in within one hour. At the same time, 23.6 g of 32% sodium hydroxide solution [188 mmol NaOH] is metered in such that the pH remains constant at 11.8. After the metering in has been completed, stirring is carried out for a further hour at 10° C., the mixture is allowed to return to room temperature, and the phases are separated. A third of the aqueous phase has 9.1 g of 32% sodium hydroxide solution added to it at room temperature, as a result of which a solid precipitates out. This solid is filtered off and dried. This gives 1.8 g of yellowish solid, which, according to ¹H NMR analysis, consists of 69.2% of the title compound.

HPLC analysis (acid): 82.6% 8-[2-(4-chloro-2,6-dimethylphenyl)acetamido]-1,4-dioxaspiro[4.5]decane-8-carboxylic acid (alongside 14.1% 4-chloro-2,6-dimethylphenylacetic acid).

Ion chromatography: 7.26% sodium (theoretical value: 5.7%)

¹H NMR (600 MHz, D$_2$O): δ=1.6-1.7 (m; 2H). 1.73-1.8 (m; 2H), 1.9-2 (m; 2H), 2.05-2.13 (m; 2H), 2.3 (s; 6H), 3.7 (s; 2H), 4.03 (s; 4H), 7.12 (s; 2H) ppm.

More solid precipitates from the filtrate. After drying, this gives 3.4 g of solid, which, according to ¹H NMR analysis, consists of 67.3% of the title compound.

Both solid fractions add up to a yield of 44% of theory (scaled up to the whole batch).

A second third of the aqueous phase has 9.1 g of 32% sodium hydroxide solution added to it at 50° C., as a result of which a solid precipitates out. Stirring is carried out at 50° C. for 15 minutes, the mixture is allowed to cool to room temperature, and stirring is carried out for a further 30 minutes. The solid is filtered off and dried. This gives 9.1 g of yellowish solid, which, according to quantitative ¹H NMR analysis, consists of 67.8% of the title compound, corresponding to a yield of 76.5% of theory (scaled up to the whole batch).

Example 3

Potassium 8-[2-(4-chloro-2,6-dimethylphenyl)acetamido]-1,4-dioxaspiro[4.5]decane-8-carboxylate

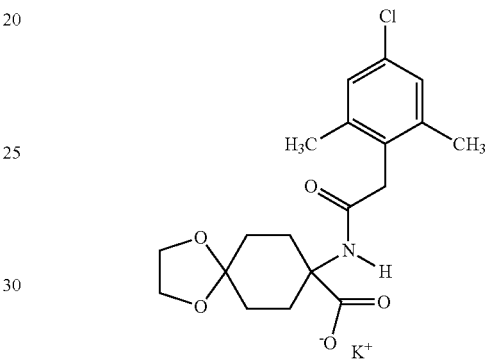

A solution of 18.84 g of potassium 8-amino-1,4-dioxaspiro[4.5]decane-8-carboxylate of a purity of 76.2% (corresponding to 60 mmol; the remainder is essentially potassium carbonate and potassium hydroxide) in 43 ml of water is initially charged in a 100 ml reaction vessel with overhead stirrer, pH electrode and metering unit. The mixture is cooled to 10° C. and the pH is adjusted to 11.8 by addition of 10% hydrochloric acid. A solution of 14.33 g [66 mmol] of (4-chloro-2,6-dimethylphenyl)acetyl chloride in 6.5 ml of toluene is subsequently metered in within one hour. At the same time, 22.9 g of 45% potassium hydroxide solution [184 mmol KOH] is metered in such that the pH remains constant at 11.8. After the metering in has been completed, stirring is carried out for a further hour at 10° C., the mixture is allowed to return to room temperature, and the phases are separated. Half of the aqueous phase has 13.7 g of 45% potassium hydroxide solution added thereto, as a result of which two phases form. The phases are separated and the lower phase (24.7 g) is concentrated under reduced pressure. This gives 15.7 g of yellowish solid, which, according to quantitative NMR analysis, consists of 67.7% of the title compound, corresponding to a yield of 84.4% of theory (scaled up to the whole batch). HPLC analysis (acid): 77.9% 8-[2-(4-chloro-2,6-dimethylphenyl)acetamido]-1,4-dioxaspiro [4.5]decane-8-carboxylic acid (alongside 12.4% 4-chloro-2,6-dimethylphenylacetic acid and 9.3% toluene). Ion chromatography: 11.6% potassium (theoretical value: 9.3%).

¹H NMR (600 MHz, D$_2$O): δ=1.5-1.6 (m; 2H). 1.65-1.7 (m; 2H), 1.8-1.9 (m; 2H), 1.95-2 (m; 2H), 2.22 (s; 6H), 3.67 (s; 2H), 4 (s; 4H), 7.09 (s; 2H) ppm.

Example 4

Methyl 8-[2-(4-chloro-2,6-dimethylphenyl)acetamido]-1,4-dioxaspiro[4.5]decane-8-carboxylate

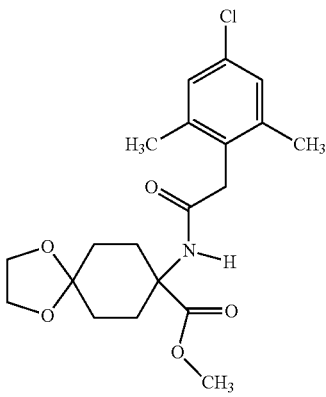 [SMILES: COC(=O)C1(NC(=O)Cc2c(C)cc(Cl)cc2C)CCC2(CC1)OCCO2]

310.0 g [0.486 mol] of a 16.6% solution of sodium carbonate in water, 15.4 g of water and 110.4 g [0.371 mol] of sodium 8-amino-1,4-dioxaspiro[4.5]decane-8-carboxylate with a purity of 75.0% (the remainder is essentially sodium carbonate and sodium hydroxide) are initially charged at room temperature into a 1000 ml reaction vessel with overhead stirrer, pH electrode, baffle and metering unit. The pH of the suspension is 13.9. The pH is adjusted to 11.8 at 20° C. by addition of 37.8 g of an 18.8% hydrochloric acid. A solution of 88.8 g [0.409 mol] of (4-chloro-2,6-dimethylphenyl)acetyl chloride in 67.6 g of toluene is subsequently metered in within three and a half hours. After the metering in has been completed, stirring is carried out for a further hour at 20° C., 166.1 g of toluene are added thereto, and the reaction mixture is heated to 80° C. At 80° C., 3.1 g [0.007 mol, purity 99%] of methyl tri-n-octylammonium chloride (Aliquat 336) are added thereto and 136.1 g [1.074 mol, purity 99.5%] of dimethyl sulfate are subsequently metered in in two hours. Before cooling to 20° C., the mixture is stirred for a further hour at 80° C. The product that precipitated out during the dimethyl sulfate metering is subsequently filtered off and the filter cake is washed twice with in each case 458 g of water and twice with in each case 176 g of toluene. After drying, this gives 115.6 g [0,285 mol] of methyl-8-[2-(4-chloro-2,6-dimethylphenyl)acetamido]-1, 4-dioxaspiro[4.5]decane-8-carboxylate with a purity of 97.6% (HPLC, external standard). This corresponds to a yield of 77%.

Example 5

Methyl 8-[2-(4-chloro-2,6-dimethylphenyl)acetamido]-1,4-dioxaspiro[4.5]decane-8-carboxylate

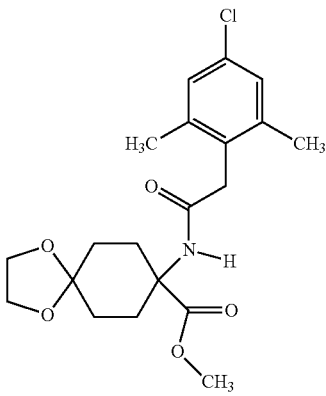 [SMILES: COC(=O)C1(NC(=O)Cc2c(C)cc(Cl)cc2C)CCC2(CC1)OCCO2]

A solution of 159.5 g [0.600 mol] of sodium 8-amino-1,4-dioxaspiro[4.5]decane-8-carboxylate of a purity of 80.4% (the remainder is essentially sodium carbonate and sodium hydroxide) in 441.8 ml of water is initially charged in a 1000 ml reaction vessel with overhead stirrer, pH electrode and metering unit. The pH of the slightly cloudy solution is 13.3. The mixture is cooled to 10° C. and the pH is adjusted to 11.8 by addition of 8.2 g of 31% hydrochloric acid. A solution of 130.0 g [0.599 mol] of (4-chloro-2,6-dimethylphenyl)acetyl chloride in 113.4 g of toluene is subsequently metered in within two and a half hours. At the same time, 86.9 g [0.695 mol NaOH] of 32% sodium hydroxide solution is metered in such that the pH remains constant at 11.8. After the metering in has been completed, stirring is carried out for a further hour at 10° C. and during this the pH is kept at 11.8 by further addition of 32% sodium hydroxide solution. The reaction mixture is heated to 20° C. At 20° C., 24.6 g [0.060 mol, purity 99%] of methyl-tri-n-octylammonium chloride are added thereto, and 153.0 g of dimethyl sulfate [1.201 mol, purity 99.0%] are metered in in one and a half hours. In parallel to the dimethyl sulfate metering, 23.0 g [0.184 mol NaOH] of 32% sodium hydroxide solution is metered in such that the pH remains constant at 11.8. The reaction mixture is stirred for a further hour and a half at 20° C. and during this the pH is kept at 11.8 by further addition of 32% sodium hydroxide solution. In the phase of further stirring, the reaction mixture has 146.1 g of toluene added thereto, in order to be able to better disperse the solid forming. At the end of the further stirring period, the solid is filtered off and successively washed with 300 g of water and three times with in each case 150 g of toluene. After drying the solid, this gives 214.3 g [0.482 mol] of the desired product with a purity of 89.1% (HPLC, external standard). This corresponds to a yield of 80%.

Example 6

11-(4-Chloro-2,6-dimethylphenyl)-12-hydroxy-1,4-dioxa-9-azadispiro[4.2.48.25]tetradec-11-en-10-one

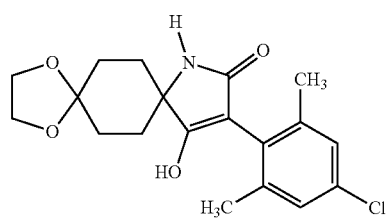 [SMILES: Cc1cc(Cl)cc(C)c1C1=C(O)C2(CCC3(CC2)OCCO3)NC1=O]

4.9 g [12.37 mmol] of methyl-8-[2-(4-chloro-2,6-dimethylphenyl)acetamido]-1,4-dioxaspiro[4.5]decane-8-carboxylate in 20 ml of anhydrous N,N-dimethylformamide are initially charged and 5.57 g [30.9 mmol] of a 30% solution of NaOMe in methanol are then added thereto. The reaction mixture is heated for three hours at 80° C. and the methanol is distilled off. Stirring is subsequently carried out for a further 16 hours at 110° C. The reaction mixture is stirred in at room temperature to a mixture of 100 ml of water and 25 ml of glacial acetic acid. The precipitated solid is filtered off with suction, washed twice with water and dried. This gives 4.4 g of a light beige solid with a purity of 97.3% according to HPLC analysis. This corresponds to a yield of 95% of theory.

The invention claimed is:

1. A process for preparing a compound of formula (I)

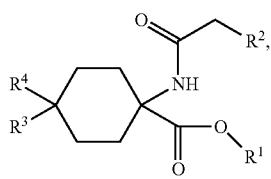
(I)

wherein
R$^1$ is straight-chain or branched C$_1$-C$_6$ alkyl or benzyl,
R$^2$ is straight-chain or branched C$_1$-C$_6$ alkyl or phenyl optionally substituted by methyl, ethyl, fluorine, chlorine, methoxy or ethoxy,
R$^3$ and R$^4$ independently of one another are an OR$^5$ or SR$^5$ radical or together are an —O(CHR$^6$)$_n$O— radical or together are an =NR$^7$ radical,
wherein
R$^5$ is straight-chain or branched C$_1$-C$_6$ alkyl,
R$^6$ is hydrogen, methyl, ethyl or phenyl,
n is 2 or 3,
R$^7$ is straight-chain or branched C$_1$-C$_6$ alkyl, phenyl, benzyl or 4-methoxybenzyl,
comprising reacting a compound of formula (II)

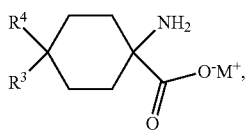
(II)

wherein
M is sodium, potassium or an NR$^8{}_4$ group,
wherein
R$^8$ is hydrogen or straight-chain or branched C$_1$-C$_6$ alkyl
with a compound of formula (III)

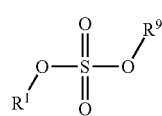
(III)

wherein
Y is fluorine, chlorine or bromine,
to give a compound of formula (IV)

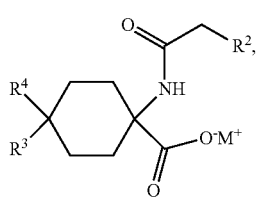
(IV)

in the presence of a base and a solvent or solvent mixture, which is not polar aprotic, and subsequent thereto the compound of formula (IV) is reacted with an alkylating reagent of formula (V) or (VI)

R$^1$—Z (V)

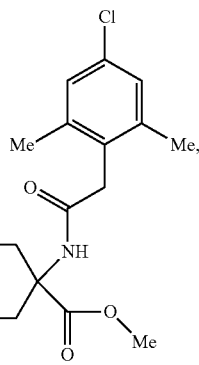
(VI)

wherein
Z is chlorine, bromine or iodine
and
R$^9$ is hydrogen, sodium, potassium or the radical R$^1$,
in the presence of a base and a solvent or solvent mixture, which is not polar aprotic.

2. The process according to claim 1, wherein
R$^1$ is methyl, ethyl, n-propyl, n-butyl or benzyl,
R$^2$ is phenyl, optionally substituted by methyl, ethyl, chlorine, methoxy or ethoxy,
R$^3$ and R$^4$ independently of one another are an OR$^5$ radical or together are an —O(CHR$^6$)$_n$O— radical or together are an =NR$^7$ radical,
R$^5$ is straight-chain C$_1$-C$_6$-alkyl,
R$^6$ is hydrogen, methyl, ethyl or phenyl,
n is 2 or 3,
R$^7$ is straight-chain or branched C$_1$-C$_6$ alkyl, phenyl, benzyl or 4-methoxybenzyl,
M is sodium or potassium,
Y is fluorine or chlorine,
Z is chlorine, bromine or iodine,
R$^9$ is hydrogen, sodium, potassium or the radical R$^1$.

3. The process according to claim 1, wherein
R$^1$ is methyl, ethyl, n-propyl or n-butyl,
R$^2$ is phenyl, optionally substituted by methyl, ethyl or chlorine,
R$^3$ and R$^4$ are an OR$^5$ radical or together are an —O(CH$_2$)$_2$O— radical,
R$^5$ is methyl, ethyl, n-propyl or n-butyl,
M is sodium or potassium,
Y is chlorine,
Z is bromine or iodine,
R$^9$ is hydrogen, sodium, potassium or the radical R$^1$.

4. A process for preparing a compound of formula (I-1)

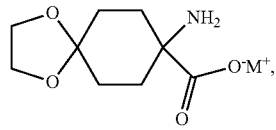
(I-1)

comprising reacting a compound of formula (II-1)

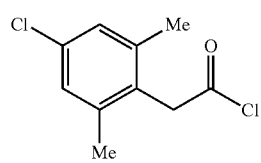
(II-1)

wherein
M is sodium or potassium,
with a compound of formula (III-1)

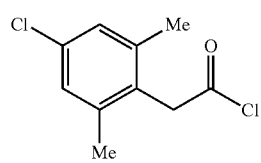
(III-1)

to give a compound of formula (IV-1)
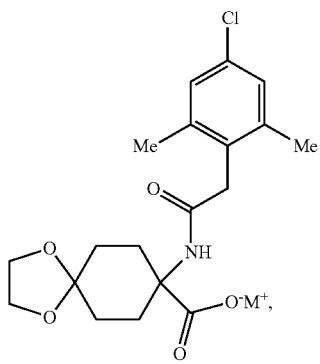
(IV-1)
wherein
M is sodium or potassium,
in the presence of a base and a solvent or solvent mixture, which is not polar aprotic, and subsequent thereto the compound of formula (IV-1) is reacted with dimethyl sulfate in the presence of a base and a solvent or solvent mixture, which is not polar aprotic.
* * * * *